United States Patent [19]

Bahr et al.

[11] Patent Number: 5,492,691
[45] Date of Patent: *Feb. 20, 1996

[54] METHOD OF MAKING CLEAR ANTIPERSPIRANT GELS

[75] Inventors: Bradley C. Bahr; Gary E. Legrow; Dimitris E. Katsoulis, all of Midland; Janet M. Smith, Bay City, all of Mich.

[73] Assignee: Dow Corning Corporation, Midland, Mich.

[ * ] Notice: The term of this patent shall not extend beyond the expiration date of Pat. No. 5,455,026.

[21] Appl. No.: 206,700

[22] Filed: Mar. 7, 1994

Related U.S. Application Data

[63] Continuation-in-part of Ser. No. 189,526, Jan. 31, 1994, Pat. No. 5,455,026.

[51] Int. Cl.$^6$ ........................................................ A61K 7/32
[52] U.S. Cl. .................................. 404/65; 424/66; 424/68
[58] Field of Search .................................. 424/68, 66, 65

[56] References Cited

U.S. PATENT DOCUMENTS 4,822,602  4/1989  Sabatelli .................................... 424/65

FOREIGN PATENT DOCUMENTS 491010    8/1990   Japan .
WO/9323008 11/1993  WIPO ..................................... 424/66

OTHER PUBLICATIONS

Van Nostrand's Scientific Encyclopedia, Seventh Edition, 1989.

*Primary Examiner*—Ceila Chang
*Assistant Examiner*—Evelyn Huang
*Attorney, Agent, or Firm*—James L. DeCesare

[57] ABSTRACT

A clear antiperspirant gel is made by combining and mixing together (A) an astringent compound having a refractive index of 1.48 to 1.53 which is an antiperspirant salt in the form of (i) a tray dried compound, (ii) an encapsulated salt, or (iii) a solvent solution of a salt compound; and (B) a clear anhydrous organic oil free gel formed with a gelator which is 12-hydroxystearic acid or its metal salts, and an aromatic containing silicone fluid or blend of silicone fluids.

2 Claims, No Drawings

METHOD OF MAKING CLEAR ANTIPERSPIRANT GELS

RELATED PATENT APPLICATION

This application is a continuation-in-part of our prior application U.S. Ser. No. 08/189,526, filed on Jan. 31, 1994, now U.S. Pat. No. 5,455,026 and entitled "Method of Making Clear Antiperspirant Gels". The prior application is assigned to the Dow Corning Corporation, Midland, Mich. USA, the same assignee as the present application.

BACKGROUND OF THE INVENTION

This invention is directed to a clear gel suitable for use as an antiperspirant which includes an aromatic containing silicone fluid.

Recent trends in consumer buying has shifted in its emphasis to a demand for clear products. These products may range from fuels for automotive vehicles to household and personal care items including dish washing and laundry detergents, as well as skin and hair care products in the form of lotions, solutions, and gels. One is apt to find on store shelves such consumer items as clear shampoos, clear sunscreens, clear bath oils, clear deodorants, and clear dentifrices. Consumers tend to equate clarity with environmental friendliness and purity, and therefore the demand for clear products is likely to continue.

It is difficult to produce a clear product. Not all of the basic ingredients necessary to formulate a clear product lend themselves to clarity, particularly when they are combined with other of the necessary ingredients in the formulated product. This is especially true in the formulation of antiperspirant gels.

Thus, the problem sought to be solved by the present invention is the production of a clear gel product suitable for use as an antiperspirant. This problem is solved according to the invention by combining only "certain" basic ingredients into the formulation which meet "certain" criteria.

The benefits and advantages derived from the invention are that a product which is effective as an antiperspirant can effectively be produced which will meet consumer demands for clarity in the marketplace.

SUMMARY OF THE INVENTION

In order to produce a clear antiperspirant gel according to this invention, several essential criteria must be present.

First, when the aromatic group on silicon is phenyl, the aromatic containing silicone which is used as the fluid to be gelled must have a viscosity of less than fifty centistokes, a molecular weight of less than 1,000, a refractive index of 1.48 to 1.53, and at least two aromatic groups as substituents on silicon atoms, with the remaining substituents on silicon atoms of the silicone fluid being methyl groups.

When the aromatic group on silicon is other than phenyl, such as a methylstyrene silicone, the aromatic containing silicone which is used as the fluid to be gelled must have a refractive index of 1.48 to 1.53.

In those instances where two or more silicone fluids are blended, the refractive index of the blend must have a value of 1.48 to 1.53.

Second, the gelator used to gel the silicone fluid is either (i) 12-hydroxystearic acid or a metal salt of 12-hydroxystearic acid. The acid is a $C_{18}$ straight-chain fatty acid with an OH group attached to the carbon chain. The acid has the formula $CH_3(CH_2)_5CH(OH)(CH_2)_{10}COOH$.

Third, the refractive index of any astringent antiperspirant compound used in the formulation has a refractive index which matches the refractive index of the aromatic containing silicone fluid, or in other words a refractive index of 1.48 to 1.53.

Fourth, the astringent antiperspirant compound must be an antiperspirant salt having a refractive index of 1.48 to 1.53. Such a compound is provided by employing an antiperspirant salt which is (i) a tray dried astringent antiperspirant salt compound; (ii) an encapsulated astringent antiperspirant salt compound; or (iii) a solution of an astringent antiperspirant salt compound in a solvent such as ethanol or propylene glycol. As used herein, the terms "tray dried" and "air dried" are considered synonymous.

By meeting the above criteria, a product can be produced which provides a satisfactory solution to the problem to be solved.

These and other features, objects, and advantages of the present invention will become more apparent from a consideration of the following detailed description thereof.

DETAILED DESCRIPTION OF THE INVENTION

The gelator is 12-hydroxystearic acid or a metal salt of 12-hydroxystearic acid. The acid has the formula $CH_3(CH_2)_5CH(OH)(CH_2)_{10}COOH$. Metal salts of 12-hydroxystearic acid can also be employed as gelator. Such salts have the formula $[C_6H_{13}-CH(OH)-(CH_2)_{10}-COO]_nM$ in which M indicates a metal such as Li+, Na+, K+, Rb+, Cs+, Mg(2+), Ca(2+), Sr(2+), Ba(2+), Mn(2+), Ni(2+), Cu(2+), Zn(2+), Cd(2+), Hg(2+), and Pb(2+); and the value of n is one for monovalent cations and two for divalent cations. An example of metal salts suitable for use according to the invention are calcium 12-hydroxystearate and lithium 12-hydroxystearate. These metal salts can be prepared by the direct neutralization of 12-hydroxystearic acid with a metal base such as sodium hydroxide or potassium hydroxide. The metal salts can also be prepared by a metathesis reaction of a simple metal salt such as sodium 12-hydroxystearate with a metal sulfate salt or a metal chloride salt such as zinc chloride or copper sulfate.

The astringent antiperspirant salt compound used in the present invention is an inorganic or organic salt form of aluminum or zirconium including mixtures thereof. Representative compounds which may be employed are aluminum chloride, aluminum chlorohydrate, aluminum dichlorohydrate, aluminum chlorohydrex, aluminum sesquichlorohydrate, aluminum-zirconium chlorohydrate, aluminum-zirconium trichlorohydrate, aluminum-zirconium pentachlorohydrate, aluminum-zirconium octachlorohydrate, aluminum-zirconium chlorohydroglycine, aluminum-zirconium tetrachlorohydrexglycine, zirconium chlorohydrate, and zirconium hydroxychloride.

The most preferred astringent antiperspirant salt compounds according to this invention are encapsulated aluminum chlorohydrate and air dried aluminum chlorohydrate.

As indicated above, the refractive index of the astringent antiperspirant salt compound matches the refractive index of the aromatic containing silicone fluid which has a refractive index of 1.48 to 1.53.

The aromatic containing silicone fluid which is used according to the present invention is a compound having one of the following formulas:

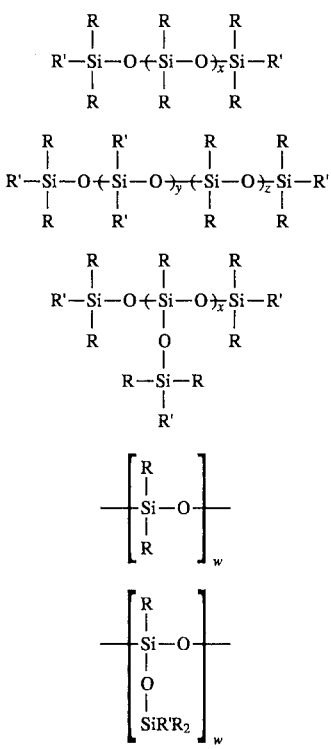

In formulas (I) to (V), R is R', an aromatic radical such as a phenyl radical, or an aralkyl radical such as 2-phenylethyl, 2-phenylpropyl, and 2-phenlybutyl; R' is an alkyl radical having from one to seven carbon atoms; x is an integer having a value of zero to one thousand; w is an integer having a value of three to six; y and z are integers the sum of which is between two and one thousand. For purposes of this invention, R' is most preferably methyl, and R is methyl, phenyl, or 2-phenylpropyl; and x has a value of 1 to 1,000.

The aromatic containing silicone used as the fluid to be gelled is most preferably phenyl substituted, has a viscosity of less than fifty centistokes, a molecular weight of less than 1,000, a refractive index of 1.48 to 1.53, and at least two phenyl groups as substituents on silicon atoms, with the remaining substituents on silicon atoms being methyl groups.

Representative of aromatic containing silicones including phenyl substituted and 2-phenylpropyl functional fluids which can be used according to the concepts of the present invention are (i) a methylphenylpolysiloxane fluid having a viscosity of twenty Centistokes measured at 25° Centigrade; (ii) a tetramethyltetraphenyltrisiloxane fluid (TMTPTS) having a viscosity of thirty-seven Centistokes measured at 25° Centigrade; (iii) a diphenyltetramethyldisiloxane fluid having a viscosity of 3.5 Centistokes measured at 25° Centigrade; (iv) a phenylmethyldimethylcyclosiloxane fluid having a viscosity of forty-five Centistokes measured at 25° Centigrade; (v) a methylstyrene-methicone fluid of the formula $(CH_3)_3SiO(CH_3RSiO)_{7.06}Si(CH_3)_3$ in which R is $-CH_2CH(CH_3)C_6H_5$ and having a viscosity of one hundred seventy Centistokes measured at 25° Centigrade; (vi) a methylstyrene-methicone fluid of the formula $(CH_3)_3SiO(CH_3RSiO)_3Si(CH_3)_3$ in which R is $-CH_2CH(CH_3)C_6H_5$ and having a viscosity of fifty-two Centistokes measured at 25° Centigrade; and (vii) a copolymeric methylstyrene-methicone fluid of the formula $(CH_3)_3SiO[(CH_3)_2SiO]_4(CH_3RSiO)_{4.5}Si(CH_3)_3$ in which R is $-CH_2CH(CH_3)C_6H_5$ and having a viscosity of forty-eight Centistokes measured at 25° Centigrade. Chemically, fluids (v) and (vi) are poly(2-phenylpropylmethylsiloxane), and fluid (vii) is Poly(2-phenylpropylmethylsiloxane-dimethylsiloxane).

These aromatic containing silicone fluids can be used alone, or as blends by combining two or more of the fluids as blended mixtures. In addition, one or more of the aromatic containing silicone fluids can be combined with other types of silicone fluids such as a volatile silicone. Where two or more silicone fluids are blended, at least one of the fluids should have at least two phenyl groups or two aralkyl groups as substituents on silicon atoms with the remaining substituents on silicon atoms being methyl groups. Furthermore, the refractive index of the blend should have a value of 1.48 to 1.53.

Methods of making aromatic silicone fluids are known in the art. Representative methods can be found in U.S. Pat. Nos. 3088964, 3186944, 3221040, and 3839384. Phenylpropylalkylcyclosiloxanes can be made according to a method described in an article entitled "Addition of Silicon Hydrides to Olefinic Double Bonds. IV. The Addition to Styrene and alpha-Methylstyrene", by John L. Speier and John W. Ryan, Journal of Organic Chemistry, Volume 24, Pages 2052–2053, December 1959. Generally such methods involve either (i) hydrolyzing phenylpropylmethylsiloxanes, or (ii) reacting alpha-methylstyrene with an organosiloxane containing ≡SiH groups in the molecule.

A volatile silicone suitable for use in a blend according to present invention should be a low viscosity methylsilicone fluid. Volatile low viscosity methylsilicone fluids correspond to the average unit formula $(CH_3)_aSiO_{(4-a/2)}$ wherein a is an integer having an average value of from two to three. The methylsilicone fluid contains siloxane units joined by Si—O—Si bonds. Representative units are $(CH_3)_3SiO_{1/2}$, $(CH_3)_2SiO_{2/2}$, $(CH_3)SiO_{3/2}$, and $SiO4/2$. These units are present in molar amounts such that there is provided an average of from about two to three methyl groups per silicon atom in the methylsilicone fluid, whereby the methylsilicone fluid has a viscosity of less than about one hundred centistokes measured at twenty-five degrees Centigrade.

The volatile low viscosity methylsilicone fluid contains dimethylsiloxane units and optionally contains trimethylsiloxane units. Preferably, the methylsilicone fluid has a viscosity of less than about ten centistokes. Representative compounds are cyclopolysiloxane compounds of the general formula $[(CH_3)_2SiO]_x$, and linear siloxane compounds of the formula $(CH_3)_3SiO[(CH_3)_2SiO]_ySi(CH_3)_3$, in which x is an integer having a value of from three to ten, and y is an integer having a value of from zero to about ten.

Volatile low viscosity methylsilicones generally have boiling points less than about two hundred-fifty degrees Centigrade, and have viscosities generally less than about ten centistokes measured at twenty-five degrees Centigrade. Most preferably, the viscosity is 0.65 to 5.0 centistokes. Volatile cyclopolysiloxane compounds have been assigned the adopted name "CYCLOMETHICONE" by The Cosmetics, Toiletries and Fragrance Association, Inc., Washington, D.C. (CTFA). Both the cyclopolysiloxanes and the linear siloxanes are clear fluids, and are essentially odorless, nontoxic, nongreasy and nonstinging. Cosmetically, these methylsilicone fluids are nonirritating to skin, and exhibit enhanced spreadability and ease of rub-out when applied. Once applied, the materials evaporate leaving behind no residue.

Methylsilicone fluids which are useful in accordance with the present invention leave substantially no residue after thirty minutes at room temperature when one gram of fluid is placed at the center of a No. 1 circular filter paper having a diameter of 185 mm supported at its perimeter in open room atmosphere. By methylsilicone fluid is meant a composition containing two or more silicon atoms, all of which are bonded by way of at least one oxygen atom to at least one other silicon atom and at least one methyl radical, each silicon valence not satisfied by oxygen being satisfied by a methyl radical.

Representative methylsilicone fluids found to be especially useful in accordance with the present invention are hexamethyldisiloxane which has a boiling point of 99.5 degrees Centigrade and the formula $Me_3SiOSiMe_3$; octamethyltrisiloxane which has a boiling point of 152 degrees Centigrade and the formula $Me_3SiOMe_2SiOSiMe_3$; hexamethylcyclotrisiloxane which has a boiling point of 133 degrees Centigrade and the formula $[(Me_2)SiO]_3$; octamethylcyclotetrasiloxane which has a boiling point of 171 degrees Centigrade and the formula $[(Me_2)SiO]_4$; and decamethylcyclopentasiloxane (DMCPS) which has a boiling point of 205 degrees Centigrade and the formula $[(Me_2)SiO]_5$.

These methylsilicone fluids may be used alone, or can be blended together as mixtures of two or more of the fluids. Mixtures of the methylsilicone fluids will result in a volatile silicone material having an evaporating behavior different from any one of the individual methylsilicone fluids.

The procedure for making the clear antiperspirant gel according to the invention is simply a matter of combining and mixing together two components, one of which is (A) 0.1 to 25.0 percent by weight of the appropriate astringent salt compound which has a refractive index of 1.48 to 1.53. The astringent salt compound is mixed with (B) a clear anhydrous organic oil free gel that has been formed from 0.1 to 10.0 percent by weight of 12-hydroxystearic acid or a metal salt of 12-hydroxystearic acid as the gelator, and 30.0 to 98.0 percent by weight of the appropriate aromatic containing silicone or the blend of fluids to be gelled. The mixture is heated to dissolve the gelator. The gel is formed when the mixture is cooled or allowed to cool.

The invention will be illustrated in more detail in the following examples and tables. An explanation of the procedures used in these examples precedes the examples.

Gel samples were prepared in one-half ounce glass vials which fit into an Orbeco-Hellige Series 965 Digital Direct-Reading Turbidimeter. The gel formulas were prepared and cast into the sample cells, allowed to set overnight or longer, measured on the turbidimeter by inserting the cell into the sample well, and recording the reading. The measurements are shown in Nephelometric Turbidity Units (NTU). The readings were all taken in the 000–999 NTU range which was calibrated daily. Readings of less than 400 NTU are considered clear; greater than 400 NTU are considered translucent; and readings under 100 NTU are considered water clear. The same samples prepared for turbidity were measured for penetration once the turbidity measures were recorded. The instrument was a Precision Penetrometer fitted with a Humboldt H1310 wax needle. The needle was lowered to the surface of the gel, the clutch released for five seconds, and the reading recorded in millimeters. Refractive indices (RI) were measured on a Bausch & Lomb Refractometer at 25° C. unless noted otherwise.

EXAMPLE 1

7.55 grams of twenty centistoke methylphenylpolysiloxane fluid having a RI of 1.46 was added to 8.05 grams of tetramethyltetraphenyltrisiloxane having a viscosity of 37 centistokes and a RI of 1.56 resulting in a blend that had a RI of 1.510. 0.60 grams of 12-hydroxystearic acid was added to the blend and heated until the gellant dissolved. The solution gelled upon cooling. The turbidity of the gel measured 140 NTU.

EXAMPLE 2

5.98 grams of the same methylphenylpolysiloxane in Example 1 was added to 6.22 grams of tetramethyltetraphenyltrisiloxane resulting in a solution with a RI of 1.510. 0.60 grams of 12hydroxystearic acid was added to the blend and heated until the gellant dissolved. 3.2 grams of an encapsulated aluminum chlorohydrate was dispersed into the solution. The solution was placed in an ice bath and gelled upon cooling. The turbidity was 240 NTU.

EXAMPLE 2b

Preparation of encapsulated aluminum chlorohydrate used in Example 2 consisted of adding 40.0 grams of stearic acid to 2000 grams of cyclomethicone and heating with stirring to 80° C. 1000 grams of a 50% aluminum chlorohydrate solution $[Al_2(OH)_5Cl.XH_2O]$ was heated to greater than 80° C. and slowly added to the cyclomethicone solution while stirring. The dispersion was heated and stirred until it reached 125° C., at which point it was filtered and the salt collected and dried in a desiccator. The collected salt consisted of spherical particles essentially ranging from 110 to 150 microns in diameter. Elemental analysis indicated 23.3% Al, 16.2% $C_{1,\ 0.43}$% C, and 4.07% H, with a metal/chlorides ratio of 1.89. The RI of this salt was 1.510.

EXAMPLE 3

6.21 grams of methylphenylpolysiloxane as in Example 1 was added to 7.59 grams of tetramethyltetraphenyltrisiloxane resulting in a solution with a RI of 1.514. 0.60 grams of 12-hydroxystearic acid was added to the blend and heated until the gellant dissolved. 1.6 grams of aluminum chlorohydrate that was air dried from a 50% solution and ball milled was dispersed into the solution. The solution was placed in an ice bath and gelled upon cooling. The turbidity was measured at 272 NTU. The RI of the salt used was 1.514.

EXAMPLE 4

3.7 grams of octamethylcyclotetrasiloxane was added to 8.8 grams of tetramethyltetraphenyltrisiloxane resulting in a solution with a RI of 1.507. 0.50 grams of 12-hydroxystearic acid was added to the blend and heated until the gel dissolved. Three grams of controlled particle size powdered spray dried aluminum chlorohydrate $[Al_2(OH)_5Cl.XH_2O]$ was dispersed into the solution. The solution was placed in an ice bath and gelled upon cooling. The turbidity was measured at 1,000 NTU. The RI of the salt was 1.521.

EXAMPLE 5

17.9 grams of diphenyltetramethyldisiloxane having a viscosity of 3.5 centistokes and a RI of 1.517 was blended with 22.9 grams of phenylmethyldimethylcyclosiloxane having a viscosity of 45 centistokes and a RI of 1.578, resulting in a blend with a RI of 1.514. 2.2 grams of myristyl dimethicone $[Me_3SiO—(Me_2SiO)_3(C_{14}H_{29}MeSiO)_6SiMe_3]$ was added as well as 2.0 grams of 12-hydroxystearic acid, and the mixture was heated until the gelator dissolved. 5 grams of aluminum chlorohydrate that was air dried and milled was dispersed into the solution. The solution was placed into an ice bath and gelled upon cooling. The turbidity was 340 NTU. The RI of the salt was 1.514.

EXAMPLE 6

Six blends of tetramethyltetraphenyltrisiloxane and decamethylcyclopentasiloxane fluids with different refractive indices were gelled with 12-hydroxystearic acid to determine how the refractive indices of the fluid effected the clarity of the gelled fluid. The ingredients were combined and heated to dissolution, poured into containers and cooled. Gels formed upon cooling. Turbidities of the gels and the blends are shown in Table I.

TABLE I

| Component | A | B | C | D | E | F | G | H |
|---|---|---|---|---|---|---|---|---|
| 12-OH stearic acid | 3 | 3 | 3 | 3 | 3 | 3 | 3 | 3 |
| TMTPTS | 100 | 80 | 75 | 70 | 65 | 60 | 50 | — |
| DMCPS | — | 20 | 25 | 30 | 35 | 40 | 50 | 100 |
| refractive index @ 21° C. | 1.558 | 1.526 | 1.518 | 1.510 | 1.502 | 1.494 | 1.478 | 1.3976 |
| turbidity (NTU) | 830 | 158 | 118 | 95 | 89 | 111 | 287 | 1000 |

In Table I, the amounts of the three (3) components used are shown in parts. TMTPTS indicates the phenyl fluid and DMCPS indicates the cyclic silicone.

EXAMPLE 7

Three gels were prepared using poly (2-phenylpropylmethylsiloxane) fluids as shown below in Table II. The 12-hydroxystearic acid gelator was added to the fluids, heated to dissolution, and cooled. The fluids gelled upon cooling. The first fluid was a methylstyrene-methicone fluid having the formula $(CH_3)_3SiO(CH_3RSiO)_{7.06}Si(CH_3)_3$ where R is —$CH_2CH(CH_3)C_6H_5$. Viscosity of the fluid was 170 centistokes measured at 25° C. The second fluid was a copolymeric methylstyrene-dimethicone of the formula $(CH_3)_3SiO[(CH_3)_2SiO]_4.5(CH_3RSiO)_{4.5}Si(CH_3)_3$ where R is —$CH_2CH(CH_3)C_6H_5$ and the viscosity at 25° C. was 48 centistokes. The third fluid was a methylstyrene-methicone fluid having the formula $(CH_3)_3SiO(CH_3RSiO)_3Si(CH_3)_3$ where R is —$CH_2CH(CH_3)C_6H_5$. The viscosity of the fluid was 52 centistokes at 25° C. As noted above, the first and third fluids are chemically poly(2-phenylpropylmethylsiloxane), and the second fluid is poly(2-phenylpropylmethylsiloxane-dimethylsiloxane). However, for the sake of convenience, their CTFA adopted names have been used in Table II.

TABLE II

| Components | A | B | C |
|---|---|---|---|
| 12-hydroxystearic acid | 0.5 | 0.6 | 0.6 |
| methylstyrene-methicone fluid 1 | 12 | — | — |
| methylstyrene-dimethicone fluid 2 | — | 14.4 | — |
| methylstyrene-methicone fluid 3 | — | — | 14.4 |
| Refractive index @ 21° C. | 1.522 | 1.483 | 1.5025 |
| Turbidity (NTU) | 55 | 443 | 240 |
| Penetration (mm) | 17.6 | 20.8 | 21.6 |

The amounts of the four (4) components used in Table I are shown in grams.

In Example 1, a basic blend of two aromatic containing silicones was prepared and the blend was gelled without an astringent salt. Both silicone fluids had a viscosity of less than fifty Centistokes, and at least one of the silicone fluids used to make the blend had at least two phenyl substituents on the silicon atom in the molecule. Example 2 is similar to Example 1 but includes an astringent salt as one of the components of the gel. Example 2b shows the method used to prepare the encapsulated antiperspirant salt used in Example 2. Example 3 is similar to Example 2 but a different antiperspirant salt was employed.

Example 4 is comparative and is set forth to show the relatively poor results obtained when the RI of the astringent salt does not match the RI of the silicone. As noted in Example 4, a high turbidity is the result. Example 4 is not representative of this invention.

Example 5 is similar to Example 3 but other types of aromatic containing silicone fluids are employed. However, both silicone fluids had a viscosity of less than fifty Centistokes, and at least one of the silicone fluids used to make the blend had at least two phenyl substituents on the silicon atoms in the molecule. In addition, the phenyl fluid in Example 5 is a cyclic molecule. Example 5 further shows the use in the gel of another type of silicone. The silicone used was myristyl dimethicone which is a compound having the structural formula $Me_3SiO(Me_2SiO)_3(C_{14}H_{29}MeSiO)_6SiMe_3$ where Me is methyl. Other silicone compounds can be used, however, including alkylmethylsiloxanes such as polymethylstearylsiloxane. Such compounds have the formula $Me_3SiO(Me_2SiO)_x(MeRSiO)_ySiMe_3$ in which Me denotes methyl, R is $C_nH_{2n+1}$ in which n is an integer having a value of at least twelve, x is zero to 200 preferably about 3 to 70, and y is 1 to 40 preferably about 6 to 20.

Example 6 and Table I show the especially good results obtained including a very low turbidity, when the gels are prepared at RI ranges which are in accordance with this invention (B, C, D, E, F, and G); in comparison to the poor results obtained including the high turbidity, when the gels are prepared at RI ranges not according to the invention (A and H). Example 6 is further exemplary of an embodiment of the invention in which an aromatic containing silicone is blended with a volatile cyclic methylsilicone fluid. This blend is formed using a ratio of aromatic containing silicone (TMTPTS) to volatile silicone (DMCPS) of from 4:1 to 1:1. As in the other preceding examples, both silicone fluids had a viscosity of less than fifty Centistokes, and at least one of the silicone fluids used to make the blend had at least two phenyl substituents on the silicon atoms in the molecule.

Example 7 and Table II show that clear gels can be obtained by using aromatic containing silicones which have in the molecule an aromatic group other than phenyl. Thus, the gels in Example 7 were prepared with aralkyl (arylalkyl) containing fluids, more particularly 2-phenylpropyl functional polymeric and copolymeric silicone fluids. Not all of the fluids in Example 7 had a viscosity of less than fifty Centistokes.

With respect to the problem sought to be solved by the present invention which is the production of a clear gel product suitable for use as an antiperspirant, particular note should be taken of blend "D" and blend "E" in Table I, and gel "A" in Table II. Blend "D" and blend "E" in Table I, and gel "A" in Table II, each exhibited a turbidity of less than one hundred NTU, which as explained above, is considered "water clear".

Other variations and modifications may be made in the compounds, compositions, and methods described herein without departing from the essential features and concepts of the present invention.

The forms of the invention described herein are exemplary only and are not intended as limitations on the scope of the invention as defined in the appended claims.

That which is claimed is:

1. A method of making a clear antiperspirant gel having a turbidity less than 400 NTU comprising forming a mixture of (A) 0.1 to 25.0 percent by weight of an astringent compound having a refractive index of 1.48 to 1.53, the astringent compound being an antiperspirant salt in a form selected from the group consisting of (i) a tray dried astringent salt compound, (ii) an encapsulated astringent salt compound, and (iii) a solvent solution of an astringent salt compound; and (B) a clear anhydrous organic oil free gel formed from 0.1 to 10.0 percent by weight of a gelator of metal salts of 12-hydroxystearic acid, and 30.0 to 98.0 percent by weight of a blend of an aromatic containing silicone and a volatile silicone, the aromatic containing silicone having a viscosity of less than fifty centistokes, a molecular weight of less than 1,000, a refractive index of 1.48 to 1.53, and at least two aromatic groups as substituents on silicon atoms with remaining substituents on silicon atoms being methyl groups; the volatile silicone in the blend being a compound selected from the group consisting of cyclopolysiloxanes of the formula $[(CH_3)_2SiO]_x$, and linear siloxane compounds of the formula $(CH_3)_3SiO[(CH_3)_2SiO]_ySi(CH_3)_3$, in which x is an integer having a value of from three to ten, and y is an integer having a value of from zero to ten; the aromatic containing silicone and volatile silicone being blended in a ratio of 4:1 to 1:1, respectively; heating the mixture to dissolve the gelator; and allowing the mixture to cool.

2. A clear antiperspirant gel formed according to the method of claim 1.

* * * * *